United States Patent [19]
Ross et al.

[11] Patent Number: 5,500,209
[45] Date of Patent: Mar. 19, 1996

[54] DEODORANT AND ANTIPERSPIRANT COMPOSITIONS CONTAINING POLYAMIDE GELLING AGENT

[75] Inventors: Lloyd Ross, Hampton; Michael S. Mendolia, Bridgewater; Anthony Esposito, Roselle; James A. Tassoff, West Caldwell; Paul J. Fessock, South Plainfield; Morton L. Barr, East Brunswick; Paul J. Vincenti, Jefferson, all of N.J.

[73] Assignee: The Mennen Company, Morristown, N.J.

[21] Appl. No.: 214,111

[22] Filed: Mar. 17, 1994

[51] Int. Cl.⁶ .................................................. A61K 7/32
[52] U.S. Cl. ................................. 424/66; 424/68
[58] Field of Search ........................... 424/66, 68

[56] References Cited

U.S. PATENT DOCUMENTS

| | | | |
|---|---|---|---|
| 3,148,125 | 9/1964 | Striance et al. | 167/85 |
| 3,341,465 | 9/1967 | Kaufman | 252/316 |
| 3,574,822 | 4/1971 | Shepherd | 424/47 |
| 3,645,705 | 2/1972 | Miller et al. | 44/7.5 |
| 4,275,054 | 6/1981 | Sebag et al. | 424/65 |
| 4,383,988 | 5/1983 | Teng | 424/68 |
| 4,425,327 | 1/1984 | Moller et al. | 424/65 |
| 4,673,570 | 6/1987 | Soldati | 424/66 |
| 4,863,721 | 9/1989 | Beck et al. | 424/47 |
| 4,937,069 | 6/1990 | Shin | 424/66 |
| 4,944,937 | 7/1990 | McCall | 424/65 |
| 4,948,578 | 8/1990 | Burger et al. | 424/68 |
| 5,019,375 | 5/1991 | Tanner et al. | 424/66 |
| 5,069,897 | 12/1991 | Orr | 424/66 |
| 5,102,656 | 4/1992 | Kasat | 424/66 |

FOREIGN PATENT DOCUMENTS

| | | | |
|---|---|---|---|
| 54-140714 | 11/1979 | Japan. | |
| WO93/24105 | 5/1993 | WIPO | A61K 7/42 |

*Primary Examiner*—C. Warren Ivy
*Assistant Examiner*—Evelyn Huang
*Attorney, Agent, or Firm*—Antonelli, Terry, Stout & Kraus

[57] ABSTRACT

Disclosed is a gel or stick composition for reduction of body malodor, containing active deodorant and/or antiperspirant ingredients, a polyamide gelling agent and a solvent system for the polyamide gelling agent. The polyamide gelling agent has good stability, even in the presence of acidic antiperspirant metal salts, and can provide a clear deodorant or antiperspirant gel or stick. The composition has good pay-off characteristics and application properties, and good structural integrity. Moreover, the composition can be formulated so as not to leave any undesirable residue, such as a white residue left after applying conventional antiperspirant sticks.

49 Claims, No Drawings

DEODORANT AND ANTIPERSPIRANT COMPOSITIONS CONTAINING POLYAMIDE GELLING AGENT

BACKGROUND OF THE INVENTION

The present invention is directed to a composition for combatting body malodor, in stick or gel form, having an active ingredient (for example, an active deodorant material, an active antiperspirant material, etc.) incorporated therein. The composition of the present invention can be used to combat body malodor, e.g., in axillary regions of the human body, by applying the composition to the human body (e.g., to the skin, in axillary regions of the body).

The present invention is particularly directed to antiperspirant compositions in stick or gel form. More particularly, the present invention is directed to a gel or stick composition including a gelling agent, and having an active ingredient (for example, an active antiperspirant material) incorporated therein, especially wherein the gelling agent is stable even in the presence of acidic active antiperspirant materials. The present composition can, preferably, be translucent or clear, but need not be translucent or clear (that is, it can be opaque). Compositions according to the present invention can even be white-opaque as is conventional antiperspirant stick compositions, using, for example, a waxy substance such as stearyl alcohol for the antiperspirant stick.

Antiperspirant products are well known in the art. Antiperspirant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes the continuous phase.

The stick form has become the dominant antiperspirant dosage form in the United States market, constituting more than 50% of total antiperspirant sales, and is popular to varying degrees globally. Cosmetically acceptable antiperspirant sticks typically consist of a suspension of spray-dried active antiperspirant material in vehicles such as cyclomethicone, with a waxy substance such as stearyl alcohol, alone or in combination with castor wax, gelling or thickening the suspension sufficiently to create a suitable stick.

The stick form can be distinguished from a gel or a paste in that in a stick, the formulated product can maintain its shape for extended time periods outside the package, the product not losing its shape significantly (allowing for some shrinkage due to solvent evaporation). One can adjust the amount of stearyl alcohol and castor wax and modify the manufacturing process to effect formation of a viscous gel or paste in place of the stick. Alternative gelling or thickening agents such as the bentones, fumed silica or polyethylene can be used in place of the wax to form the gel or paste. These gels or pastes can be suitably packaged in containers which have the appearance of a stick, but which dispense through apertures on the top surface of the package. These products have been called soft sticks or "smooth-ons". Hereinafter, these soft sticks are generically called "gels". Reference is made to U.S. Pat. No. 5,102,656 to Kasat, No. 5,069,897 to Orr, and No. 4,937,069 to Shin, each of which disclose such gels, including physical characteristics thereof such as viscosity and hardness. The contents of each of these three U.S. patents are incorporated herein by reference in their entirety.

The hard stick dosage form (hereinafter called "sticks"), although widely accepted by the consumer, suffers from leaving a white residue on skin after application, and can cause staining of fabric, which is considered to be undesirable, particularly by female consumers. The gel dosage form can be formulated to eliminate the white residue; however, the product appears initially as white and opaque, requiring consumer education and trial to fully appreciate the low-residue property. Furthermore, in gels of this type, the active ingredient is suspended in a vehicle such as cyclomethicone; in such suspensions, syneresis and creeping of the liquid is a common problem, resulting in instability of the formula or poor aesthetic properties, particularly when shipping product in warm climates and/or at high altitudes.

Illustratively, U.S. Pat. No. 3,341,465 to Kaufman, et al discloses a clear, transparent oil-in-water gel emulsion for cosmetic purposes. The emulsion disclosed therein includes water, an ester of a lower monohydric alcohol and a fatty acid, a higher fatty acid alkylolamide, polyoxyethylene ethers of higher aliphatic alcohols, and/or polyoxyethylene esters of higher fatty acids, and a compound selected from the group consisting of esters of polyhydric alcohols, such esters of polyhydric alcohol having at least one free hydroxyl group and at least one esterified fatty acid group. This patent discloses that the emulsions can include various cosmetic adjuvants including bactericides such as hexachlorophene.

Recently, there has been significant activity in developing clear and translucent antiperspirant sticks and gels. Clear or translucent antiperspirant sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional active antiperspirant materials are acidic, much work has been involved in discovering suitable stabilizing or buffering agents to prevent or slow down acid attack on the acetal gelling agent. Such work has not been completely successful. Moreover, these clear or translucent antiperspirant sticks, containing the acetal gelling agent and including a solubilized active antiperspirant material, have the disadvantage of being inherently tacky. Thus, development work in connection with these clear or translucent antiperspirant sticks containing the acetal gelling agent has focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Clear and translucent antiperspirant gels (which have been dispensed from containers having the appearance of a stick) have been marketed, consisting of viscous, high internal phase emulsions. These gels exhibit some advantages over the aforementioned acetal-based clear sticks, in that the selection of formulation ingredients is less restricted (for example, water can be used), and often tack can be reduced significantly. But these emulsions still suffer from the disadvantages of feeling cool to the skin upon application, and often require the use of ethanol, which has negative environmental regulatory implications.

U.S. Pat. No. 4,863,721 to Beck, et al discloses a polar solvent-free antiperspirant composition including specific amounts of at least one particulate cellulose ether polymer, at least one active antiperspirant material, and at least one anhydrous antiperspirant carrier. This patent discloses that the composition has a reduced tendency to sting the user since it is free of polar solvent. The composition, in stick form, includes waxy materials, and also includes an inert spherical particulate material having a mean diameter of at least about 10 microns and being essentially free of particulates having diameters greater than about 150 microns. These inert particulate materials include those comprised of polyolefins, nylon, "Teflon", insoluble cross-linked starches, and mixtures thereof.

The disclosed antiperspirant compositions of U.S. Pat. No. 4,863,721 do not avoid the above-discussed problems in connection with prior known compositions, including, e.g., the residue problems.

U.S. Pat. No. 4,275,054 to Sebag, et al discloses unsaturated polyanionic polyamides which can be used as body deodorants or as room deodorizers. The polyamides disclosed are salts of polyanionic polyamides, which can act as odor absorbers from human perspiration. This patent discloses that compositions containing at least one of the polyanionic polyamide compounds can be used in the form of, e.g., aqueous or aqueous-alcoholic solutions, emulsions, sticks, powders, creams, aerosols, gels or solid cakes.

Although disclosing incorporation of specific polyanionic polyamide salts in deodorants as odor absorbers, this patent does not each now to avoid previously discussed problems arising in known stick or gel compositions, in connection with stick or gel antiperspirant compositions, in connection with the gelling agents. This patent does not disclose use of the polyanionic polyamides as gelling agents, to cause gelation of the compositions into gels or sticks.

International (Published) Patent Application No. WO93/24105 discloses a topical antiperspirant composition consisting essentially of a non-toxic water-insoluble occlusive film-forming antiperspirant polymer as the antiperspirant active agent, so that an antiperspirant composition with reduced amounts of aluminum (or other metal) antiperspirant material can be achieved. The antiperspirant polymer can be an alkyl olefinic acid amide/olefinic acid or ester copolymer alone or in combination with a water-repellent polymer or a PVP/linear alpha-olefin copolymer; or an octylacrylamide or propenamide/acrylate copolymer alone or with a PVP/linear alpha-olefin copolymer or a PVP/Eicosene copolymer, among others. The topical antiperspirant can be in stick form; various examples show use of stearyl alcohol and/or sodium stearate as gelling/thickening agents for forming the topical antiperspirant in stick form.

This International Published Patent Application discloses the polymer (copolymer) as the antiperspirant active agent, and, in the composition in stick form, does not disclose that the polymer is a gelling/thickening agent. Other components of the composition in stick form act as the gelling/thickening agent.

U.S. Pat. No. 3,645,705 to Miller discloses transparent combustible material suitable for candle bodies, including a mineral oil and/or a natural oil as a gel base; a polyamide resin as the gelling agent; and an 8-,10- or 12- carbon primary alcohol, the primary alcohol being necessary so that the gel system burns with a satisfactory flame, and to avoid a greasy appearance and feel of the material. This patent discloses that the polyamide, which serves to gel the oil, can be one of a number of long-chain linear amide resin polymers derived from the reaction of dimerized linoleic acid with di- or polyamines, the polyamides useful for forming the material for the candle body being those having molecular weight in the range of 6,000–9,000. This patent discloses that a preferred polyamide is available commercially as a product of General Mills, sold under the trade name "Versamid" 940. The contents of U.S. Pat. No. 3,645,705 are incorporated herein by reference in their entirety.

U.S. Pat. No. 3,645,705 is concerned with providing candle body material, which achieves a desired flame and avoids a greasy appearance and feel. This disclosure, directed to a candle body, does not address the problems addressed by the present invention (for example, providing a gel or stick composition having good pay-off and aesthetic characteristics, and good stability in the presence of acidic active antiperspirant materials, yet which is low in residue).

U.S. Pat. No. 3,148,125 to Strianse, et al discloses cosmetic lipsticks which, besides carrying color for staining the lips and a vehicle for the color, have a body sufficiently strong and stable to permit its use as an applicator yet capable of rubbing off onto the lips a film adapted to color and protect the lips and to leave an attractive well-groomed appearance. The lipsticks utilize soluble or solubilized dyes, and are free from all opaque materials. The patent discloses that the structural aspects of the lipstick are based upon solid polyamide resin, which is a solid but soluble condensation product of an aliphatic dicarboxylic acid and a diamine, the carboxyl and amino groups of adjacent monounits being condensed to an amide linkage in the polymer. This patent discloses that the polyamide resin should be modified to have good properties as a lipstick by compounding with softening agents, such as polyamide solvents of the type exemplified by lower aliphatic alcohols in combination with other polyamide solvents, such as fatty acid esters, e.g., glycol esters or higher fatty acids (especially between $C_{12}$ and $C_{18}$), especially propylene glycol mono laurate, polyethylene glycol (400) mono laurate, castor oil, lauryl lactate, and fatty alcohols, e.g., oleyl alcohol. This patent discloses that oil-soluble dyes can be used directly, because of the oily nature of the vehicle; but that hydrophilic dyes can also be used.

U.S. Pat. No. 3,148,125 is concerned solely with cosmetic lipsticks, carrying color for staining the lips. This patent does not disclose stable deodorant sticks and/or gels, such as antiperspirant sticks and/or gels, particularly which are stable in the presence of acidic active antiperspirant materials. Moreover, this patent is concerned with leaving a color residue on the lips, and is not concerned with a low-residue stick or gel composition to be applied, for example, to axillary regions of the skin.

Accordingly, there is still a need for providing a stable deodorant or antiperspirant stick and/or gel, for example, an antiperspirant stick or gel, which delivers the promise of a low residue benefit to the consumer in a meaningful and unencumbered way; which can be either clear, translucent or opaque; which provides good flexibility to the formulator in developing cosmetically acceptable dosage forms; and which does not exhibit excessive syneresis.

SUMMARY OF THE INVENTION

Accordingly, it is an object of the present invention to provide a composition for combatting (reducing) body malodor, e.g., in stick or gel form, that can be opaque, translucent or clear, containing an active deodorant and/or antiperspirant ingredient and a solidifying (gelling/thickening, hereinafter "gelling") agent, which has good pay-off and aesthetic characteristics, and a method of making such composition.

It is a further object of the present invention to provide a stick or gel composition for reducing body malodor, containing an active deodorant and/or antiperspirant ingredient and gelling agent, having good structural integrity.

It is a further object of the present invention to provide a stick or gel composition for reducing body malodor, that can preferably be clear even when an active antiperspirant ingredient is incorporated therein.

It is a further object of the present invention to provide an antiperspirant stick or gel composition, wherein the active antiperspirant ingredient does not degrade the gelling agent, even where such active antiperspirant ingredient is an acidic antiperspirant metal salt, and a method of making such composition.

It is a still further object of the present invention to provide an antiperspirant stick or gel composition containing an antiperspirant metal salt, such as aluminum chlorohydrate or aluminum-zirconium tetrachlorohydrex-Gly, wherein the antiperspirant metal salt does not degrade the gelling agent (that is, the gelling agent is stable in the presence of the acidic antiperspirant metal salt).

It is a still further object of the present invention to provide an antiperspirant stick or gel composition, containing an active antiperspirant ingredient and a gelling agent, which leaves at most only a small residue, or a residue that is optically clear, after being applied to the skin.

It is a still further object of the present invention to provide an antiperspirant stick or gel composition containing an active antiperspirant ingredient and a gelling agent, wherein the composition is clear, and wherein the gelling agent is stable even in the presence of the active antiperspirant ingredient, and a method of making such composition.

It is a still further object of the present invention to provide a stick or gel composition for reducing body malodor, containing an active deodorant and/or antiperspirant ingredient and gelling agent, which does not exhibit excessive syneresis, and which is reversible (that is, which can be melted and re-cast in molds without change in the overall properties of the composition).

The foregoing objects are achieved by the present composition, which is a gel or stick, and which includes active deodorant and/or antiperspirant ingredients, a polyamide gelling agent, and a solvent for the polyamide gelling agent.

The active deodorant and/or antiperspirant ingredients are included in the composition in an amount effective to reduce body malodor (that is, in a sufficient amount to have an effect to reduce body malodor where applied). For example, where the active ingredient is a deodorant active material, such as an antimicrobial ingredient, the antimicrobial ingredient is to be included in the composition in a sufficient amount such that bacteria levels are reduced where the composition is applied, e.g., to the skin, to reduce body malodor. Similarly, where the active cosmetic ingredient is an antiperspirant material, the active antiperspirant material is to be included in the composition in an amount so as to reduce flow of perspiration where applied.

The deodorant active ingredient can be a plurality of materials, such as a deoperfume and an antimicrobial agent, in combination acting to reduce body malodor (e.g., by reducing bacteria levels and masking any malodor formed). Of course, a combination of deodorant materials (e.g., an antimicrobial agent and a deoperfume) and antiperspirant materials can be used as the active ingredient.

The polyamide is a gelling agent in the composition, such gelling agent acting to provide the composition as a gel composition (e.g., a "soft stick") or a stick composition (e.g., "hard stick"); the gelling agent forms a continuous phase of the composition. The active deodorant and/or antiperspirant ingredient can be in solution in this continuous phase; or can be dispersed in this continuous phase; or can be dissolved in a second, discontinuous phase which is emulsified in the continuous phase (forming a solid emulsion as the composition for reducing body malodor).

The polyamide gelling agent of the present invention must be soluble in a cosmetically acceptable solvent at elevated temperatures, and solidify (e.g., gel) upon cooling; acceptable solvents include (but are not limited to) various alcohols, including (but not limited to) dipropylene glycol, hexylene glycol, butylene glycol, isocetyl alcohol and oleyl alcohol.

The polyamides which are useful as gelling/thickening agents for the present invention should be soluble in suitable cosmetic solvents at room temperature or elevated temperatures (particularly at elevated temperatures, most preferably between 50°–100° C., although not limited thereto). Because of this, it is preferred that the polyamides are not extensively cross-linked covalently (which would prevent solubility). The polyamides of interest are classified as thermoplastics, rather than thermosets.

Many conventional polyamides, such as nylon 6, do not exhibit adequate solubility in the solvents of interest, and are not preferred. There are two classes of polyamides which possess enhanced solubility, and are particularly preferred as polyamides for use in the present invention: (1) those based on terpolymers of simple nylons (such as DuPont Elvamide 8061, which is a terpolymer of nylon 6, nylon 66, and nylon 610); and (2) polyamides based on complex fatty acids (such as the Versamid series of Henkel Corp. or the UniRez series of Union Camp Corp.).

As for the first class of polyamides, while the individual homopolymers may not be soluble in alcohols or alcohol/water mixtures and would not be preferred polyamides for use in the present invention, the terpolymers are in many instances sufficiently soluble and are preferred.

The above-listed second class of polyamides (that is, the polyamides based upon complex fatty acids) is the most preferred class of polyamides for use in the present invention. Polyamides based on fatty acids are described in detail and distinguished from conventional nylons, in the *Encyclopedia of polymer science and Technology*, vol. 10, page 597 (1972) and in the monograph *The Dimer Acids* (Edward C. Leonard, Ed.) (1975), the contents of each of which are incorporated herein by reference in their entirety. Patents directed to dimer acid-based polyamides include U.S. Pat. Nos. 2,379,413 and 2,450,940, the contents of each of which are incorporated herein by reference in their entirety.

This second class of polyamides are polyamides based on dimerized fatty acids. The reaction of dimer acids with difunctional amines (for example, ethylene diamine or propylene diamine) produces neutral polyamides, but the reaction of dimer acids with polyfunctional amines (for example, diethylenetriamine) produces a class of chemicals known as reactive polyamides. The reactive polyamides are not preferred in connection with the present invention; they appropriately function as curing agents (generally liquids) possessing high amine functionality, and will react at room temperature or elevated temperatures to produce an irreversibly cross-linked system.

The neutral polyamides are most preferred as gelling/thickening agents according to the present invention. The fatty acids employed as reagents are typically derived from tall oil, and illustratively (but not limiting) include oleic, linoleic and arachadonic acid. Thus, a class of useful polyamides for the present invention is those formed using a dimer of a fatty acid, such as a dimer of linoleic acid. The dimer acids used normally involve a mixture of high molecular weight components and are not purely difunctional. For example, in commercial dimer acids, typically some trimer acid is present. As a result, polymers based on dimer acids usually possess some degree of branching or cross linking. As a result, the dimer acid-based polymers typically have relatively low molecular weights. Neutral polyamides based on dimer acids, and preferred for use in the present invention, generally have molecular weights from 1,000 to 30,000 daltons (molecular weight can be determined by gel permeation chromatography (GPC), with tetrahydrofuran (THF) a typical solvent). Illustratively, but not limiting, a maximum molecular weight of polyamides to be used in the present invention is 60,000 daltons, determined as set forth in the previous sentence. Note that the cross-linking can be controlled to some extent by the use of monofunctional molecules to balance the polybasic acid present.

The neutral polyamides of particular interest here are produced from a condensation polymerization involving acids and amines. The most important reagents to produce linear polymers would be diacids and diamines; but, as mentioned earlier, typically some polyfunctional reagents (such as trimer acids) are also employed in typical polymerizations (whether deliberately to produce some branching or cross-linking, or simply because the reagents are not completely purified). By the same token, some monofunctional reagents may be employed as well (deliberately to control the molecular weight and to prevent cross-linking, or again simply because of purification). For this class of polyamides, one of the reagents preferably is a complex fatty diacid. However, other acids (for example, aliphatic or aromatic or silicon-containing mono-,di- or poly-functional acids) may be used. The amine may be any aliphatic or aromatic or heterocyclic or silicon-containing diamine (primary or secondary). In addition, various monofunctional reactants (including monofunctional alcohols, amines, acids, amino acids and hydroxy acids) can be used to modify the properties of the polyamide resins, such as solubility or tendency to gel. A combination of various acids and amines are typically used in the reagent mixture. For example, the dimer acid may be mixed with sebacic acid and reacted with ethylenediamine, to produce a copolyamide. As a ratio of sebacic acid to dimer acid increases, the melting point increases dramatically. Other diamines than ethylenediamine typically result in lower melting points.

The polyamides act as gelling agents under various conditions. Gelation may occur in systems whose polyamide concentration exceeds a certain concentration (which will vary with solvent system, and which may, in some cases, be related to the concentration at which molecular overlap is achieved) at temperatures below the melting point of the polyamide resin. The mode of gelation is thought to involve the crystallization of the polyamide, although applicants do not want to be limited to this theory. This theory is supported by several experimental observations: (1) the x-ray diffraction patterns of the gels typically include some sharp peaks, indicating the presence of some long-range order; and (2) by differential scanning calorimetry, it has been observed for some systems that the gels exhibit an endothermic event attributed to a melt at temperatures greater than room temperature, and the enthalpy of fusion of this event increases linearly with the polyamide weight fraction. If each polymer chain, on the average, is involved in at least two different crystallites, a macroscopic three-dimensional network is established, and the system acquires the dimensional stability of a solid. This gel structure is not permanent since the junction zones are crystallites rather than the covalent bonds involved in cross-linked networks; as a consequence, simply heating the gelled systems to a temperature at which the crystallites melt will return the systems to a fluid state. This type of gelation is often called thermoreversible, or physical, gelation, and is well-known for a number of homopolymer or copolymer/solvent systems (for example, polyethylene in toluene or decalin; isotactic polystyrene in carbon disulfide; and polyvinyl alcohol in water). The polyamide can be semicrystalline.

Of course, the polyamide for use in the present invention must gel (solidify the composition), upon cooling of a solution of the polyamide from elevated temperatures.

The solvent for the polyamide is an important component of the present invention. As discussed previously, such solvent must be cosmetically acceptable (that is, it must be applicable to human skin without substantial irritation). The solvent desirably is a strong hydrogen bonding material, and the polyamide dissolves in the solvent at elevated temperatures (for example, 35°–150° C.). See the chapter entitled "Solubility Parameter Values" in *Polymer Handbook,* for what is meant by a "strong" hydrogen bonding solvent material. Generally, surface active agents are strong hydrogen bonding materials, while low polarity solvents are weak hydrogen bonding materials. Polyhydric alcohols vary in their hydrogen bonding activity, but generally are strong hydrogen bonding materials.

The solvent need not be a single solvent, and can be a solvent system including at least one solvent (e.g., it can include a plurality of solvents). The solvents include, illustratively, fatty alcohols (both branched and straight-chain), polyhydric alcohols, polyorganosiloxanes such as phenylmethicones and dimethicones, esters, ethoxylated alcohols, and solvent systems of mixtures of the foregoing, and/or with silicone fluids such as cyclomethicones. Illustrative solvents, in addition to those listed elsewhere in this disclosure, include cetyl alcohol, diisopropyl sebacate, PPG-3-myristyl ether, and the previously mentioned alcohols including oleyl alcohol. Various lactate esters are also illustrative solvents usable as part of the present invention. As can be appreciated, an amount of the solvent (solvent system) is utilized such that the polyamide can be fully dissolved therein at elevated temperatures, and yet can form a gel therefrom (solidify) upon cooling.

As mentioned previously, various active ingredients (for example, active deodorant materials, active antiperspirant materials, etc.) can be incorporated as part of the composition of the present invention. Various known active deodorant materials can be incorporated in compositions of the present invention. Active deodorant materials (e.g., deodorant fragrances, odor absorbents, odor preventing agents, etc.) are described in the chapter entitled "Deodorant Ingredients" by E. P. Seitz, et al, in *Antiperspirants and Deodorants,* (K. Laden, et al Ed. 1988), pages 345–390. *Antiperspirants and Deodorants* is volume 7 of the Cosmetic Science and Technology Series. This chapter, entitled "Deodorant Ingredients" is incorporated herein by reference in its entirety. Many present-day commercial products include Triclosan as an antimicrobial agent and a fragrance, as active deodorant materials.

Conventional antiperspirant metal salts can be incorporated in the composition of the present invention. The polyamide gelling agent, as part of the gel or stick, is stable in an acidic environment, so that the stability of the composition according to the present invention, in the presence of conventional acidic antiperspirant metal salts, is greatly improved as compared to, for example, stick compositions containing an antiperspirant metal salt and gelled utilizing a dibenzylidene monosorbitol acetal gelling agent. Thus, even if an acidic antiperspirant metal salt is incorporated in the composition of the present invention, the composition is stable and can provide a clear product. Moreover, antiperspirant compositions according to the present invention can be easily formulated so as not to leave an undesirable white residue on the skin. This is a particular advantage of the present invention, since the gellant is largely in soluble form in the composition, and any crystallized particles are of sufficiently small particle size to allow transparency (avoid the white residue). Of course, if compositions of the present invention contain gelling/thickening agents other than the polyamide, such as waxes, a white residue would possibly be left on the skin.

The composition according to the present invention can include other ingredients conventionally incorporated in deodorant or antiperspirant gels and/or sticks, particularly if clarity is not a factor. As for various other ingredients which can be incorporated, attention is directed to the optional components such as hardeners, strengtheners, chelating agents, colorants, perfumes, emulsifiers and fillers, described in various patent documents listed in the following, all incorporated by reference herein in their entirety:

U.S. Pat. No. 3,255,082 to Barton;
U.S. Pat. No. 4,049,792 to Elsnau;
U.S. Pat. No. 4,137,306 to Rubino, et al;
U.S. Pat. No. 4,279,658 to Hooper, et al.

Preferably, when the composition according to the present invention is in the form of a solid emulsion, the composition includes a surfactant, to ensure that the discontinuous phase stays dispersed upon cooling the composition until the polyamide gels. Such surfactant is also preferred such that the composition can be easily rinsed from the skin.

At lower levels of polyamide included in the composition, a gel is formed. At higher levels, or when other gelling agents are included in the composition, the hardness of the composition is increased, so as to form a hard stick. It is within the present invention that the composition includes conventional gelling agents, in addition to the polyamide, so as to provide a composition with increased hardness.

Antiperspirant compositions according to the present invention, containing an active antiperspirant material as the active ingredient incorporated in the gelled polyamide, can be formulated so as not to leave an undesirable white residue on skin following application, as occurs with conventional antiperspirant sticks. The antiperspirant compositions according to the present invention may be optically clear, and can deposit a suitable amount of active antiperspirant material when the composition is rubbed on the skin (for example, in axillary regions of the body).

While optically clear gels and sticks can be achieved according to the present invention, depending on other ingredients incorporated in the composition a translucent or opaque stick or gel will be provided. Depending on other gelling/thickening agents incorporated in the composition, the stick or gel composition of the present invention can have a same appearance as currently marketed antiperspirant sticks, which appear as opaque, usually white (unless colored with dyes) waxy solids which leave a white residue on skin immediately after application.

As discussed previously, the composition according to the present invention can be formulated either as a gel or as a stick. It is difficult to quantitatively distinguish between a cosmetic "gel" and a cosmetic "stick". For example, note the discussion in the article by Schmolka, "Gel Cosmetics", in *Cosmetics &. Toiletries,* Vol. 99 (November 1984), pp. 69–76. Generally, a gel is more viscous than a liquid, or than a paste which fails to retain its shape. It is not as rigid as a stick. Typically, it is understood that gels are soft, deformable products while sticks are free-standing solids.

Almdale, et al (*Polymer Gels and Networks,* Vol. 1, No. 5 (1993)) list two criteria for defining a system as a gel: (1) a gel consists of two or more components, one of which is a liquid, present in substantial quantities; and (2) a gel is a soft, solid or solid-like material. This latter requirement can be described more accurately through rheological measurement. Typically, gels possess a storage modulus $G'(w)$ which exhibits a pronounced plateau at higher frequencies (on the order of seconds), and a loss modulus $G''(w)$ which is considerably smaller than the storage modulus in the plateau region. Many of the compositions according to the present invention, utilizing the polyamide gelling agent, are gels by the above definition. In the strict sense, the term "gel" applies to systems having a value $G'(w)$ that is higher than its value of $G''(w)$ at low frequencies; in practice, however, many products marketed as "gels" are truly viscous liquids (for example, some toothpastes). Many of the compositions according to the present invention, utilizing a polyamide gelling agent, are gels by the foregoing definition.

In the cosmetic field, systems are sometimes classified as gels or sticks, depending on their viscosity or hardness alone; typically, it is understood that gels are soft, deformable products while sticks are strictly free-standing solids. For example, by rheological analysis, a commercial deodorant stick has been determined to have a plateau storage modulus $G'(w)$ of roughly $10^3$Pa and a complex viscosity of $10^6$Pa second (both at an angular frequency of 0.1 rad/sec). On the other hand, a commercial antiperspirant gel has been determined to have a $G'(w)$ value of roughly $10^3$Pa and a complex viscosity of $10^4$Pa second (at 0.1 rad/sec).

Rheological parameters such as the storage modulus $G'(w)$ can be measured as a function of angular frequency with a parallel-plate rheometer. For example, such parameters can be generated using a Carrimed CLS 100 Rheometer, using a 2 cm stainless steel plate and a 1 mm sample gap; and over a range of 0.2 to 100 rad/sec at 25° C., using a 1% strain. The principles of rheology and their applications to cosmetic products are reviewed in *Rheological Properties of Cosmetics and Toiletries,* Dennis Laba, Ed. (1993). While gels and sticks do not necessarily have a clear distinction therebetween, for purposes of the present invention if the plateau storage modulus $G'(w)$ (typically taken at angular frequencies in the range of 10–200 rad/sec) is higher than $10^3$Pa the composition can be considered a stick Illustratively, and not limiting, an antiperspirant composition according to the present invention can be as follows, including:

(a) from 2 to 40 (preferably 6 to 20) weight percent, of the total weight of the composition, of a polyamide gellant, which is defined as a polymer that contains recurring amide groups as an integral part of the main chain;

(b) from 10 to 95 weight percent, preferably 30 to 95 weight percent, of the total weight of the composition, of a solvent for the polyamide gellant (this solvent can also serve as a cosmetic emollient);

(c) from 0 to 50 weight percent, preferably 0 to 25 weight percent, of the total weight of the composition, of a surface active agent to ensure rinsability of the composition from the skin if the solvent is not sufficiently hydrophilic;

(d) from 4 to 30 weight percent, of the total weight of the composition, of an antiperspirant active ingredient; and (e) from 0–30 weight percent, of the total weight of the composition, of water.

It is a feature of the present invention that the composition of the present invention can include water. As mentioned previously, water desirably is not incorporated in clear or translucent antiperspirant sticks gelled by dibenzylidene monosorbitol acetal, since acid hydrolysis of the gelling agent occurs more rapidly in aqueous solutions.

Compositions according to the present invention can include optional ingredients. For example, antiperspirant compositions can include optional ingredients to further enhance clarity, structural integrity, antiperspirant and/or deodorant performance, cosmetic appeal and to facilitate manufacturing. For example, the antiperspirant compositions can include, illustratively, deodorant materials, including (but not limited to) antimicrobial agents and deodorant fragrances. Auxiliary solidifying or gelling or thickening agents such as fatty alcohols containing from 16 to 55 carbon atoms, such as stearyl alcohol or behenyl alcohol; fatty acid amides such as stearamide diethanolamine [N, $N^1$-bis(2-hydroxyethyl) stearamide]; ethylene dioleamide (N, $N^1$-1,2-ethanediyl bis-9-octadecenamide); ethylene distearamide ($N,N^1$-1,2-ethanediyl bis-9-stearamide); castor wax; polyvinyl alcohols; paraffin waxes; particulate polyethylenes; fumed silicas; carbowaxes; hydroxyethyl cellulose or hydroxypropyl cellulose; polysaccharides such as guar gum; and other materials known to those skilled in the art as gellants, can be incorporated as co-gellants according to the present invention, whether in antiperspirant compositions or other cosmetic compositions. These gellants can be used at appropriate levels, usually up to 20% by weight, of the total weight of the composition. In addition, coupling agents for improved clarity, such as propylene carbonate, ethanol, phenyldimethicone, and hexyl alcohol may be useful, particularly when used at levels up to 20% by weight, of the total weight of the composition.

While in the foregoing illustration an antiperspirant composition, containing an antiperspirant active ingredient, is described, it can be appreciated that the compositions according to the present invention need not include the antiperspirant active ingredient, and can include various deodorant active ingredients, so as to provide deodorant gel or stick compositions. For example, a deodorant stick can be provided. In such deodorant stick, a fragrance would, illustratively, be included, in an amount of 0.5%–3.0% by weight, of the total weight of the composition; such deodorant stick would also preferably include an antimicrobial agent, such as Triclosan, in an amount of from 0.1% to 0.5% by weight, of the total weight of the composition.

Generally, in all of the compositions according to the present invention, the polyamide would be incorporated in the composition in an amount of from 2% to 40% by weight, of the total weight of the composition; and the solvent system would be incorporated in the composition in an amount of 10%–95% by weight, of the total weight of the composition. Furthermore, the active ingredient would be included in the composition in an amount of from 0.1% to 30% by weight, of the total weight of the composition.

Compositions according to the present invention have good structural integrity, good pay-off of the active material when the composition is rubbed on the skin, and good application properties. In addition, a desired hardness of the gel or stick can be achieved. Moreover, a desired feature of the composition utilizing the polyamide gelling agent is that the composition is reversible; that is, the composition can be melted and re-cast in molds, without change in overall properties of the composition. In addition, compositions according to the present invention have good processibility. Moreover, the compositions according to the present invention can include conventional acidic active antiperspirant materials, including conventionally used aluminum chlorohydrate and aluminum-zirconium tetrachlorohydrex-Gly; and even when incorporating such conventional active antiperspirant materials there can be provided a clear antiperspirant stick or gel composition. Furthermore, the polyamide gelling agent has good stability in the composition (in particular, has better stability than dibenzylidene monosorbitol acetal gelling agent, in antiperspirant compositions containing acidic antiperspirant metal salts). In addition, the composition can leave a decreased residue on the skin, particularly as compared with conventional antiperspirant sticks utilizing a waxy hardener.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, the present invention is described primarily in connection with an antiperspirant composition, including clear antiperspirant compositions. However, the present invention is not limited to antiperspirant compositions (i.e., need not contain an active antiperspirant material). For example, the composition according to the present invention can be a deodorant composition. Moreover, depending on the active ingredient included in the composition, the composition can also be an emollient composition, a sunscreen composition, etc. As to the various types of cosmetic sticks, and active materials incorporated therein, attention is directed to U.S. Pat. No. 4,322,400 to Yuhas, the contents of which are incorporated herein by reference in their entirety.

Throughout the present specification, "active deodorant" materials and "active antiperspirant" materials are discussed. Both types of materials contribute to reduction of body (e.g., axillary) malodor. By reduction of body malodor, we mean that, generally, there is less body malodor after application of the composition to the person's skin, as compared to the person's body malodor without application of the composition. Such reduction can be due to a masking of the malodor, absorption and/or chemical reaction of the malodorous materials, reduction of levels of the bacteria producing the malodorous materials, e.g., from perspiration, reduction of perspiration, etc. The antiperspirant materials primarily act to reduce body malodor by reducing production of perspiration; the antiperspirant materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacting with malodorous materials, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

As indicated previously, a desired feature of the present invention is that a clear, or transparent, antiperspirant stick or gel composition (e.g., antiperspirant stick or gel composition), and that a clear deodorant stick or gel composition, can be provided. The term clear or transparent (that is, clarity), according to the present invention, is intended to connote its usual dictionary definition; thus, a clear antiperspirant stick allows ready viewing of objects behind it. By contrast, a translucent antiperspirant stick, although allowing light to pass through, causes the light to be so scattered that it will be impossible to see clearly objects behind the translucent stick.

Within the context of this invention, a stick or gel (e.g., an antiperspirant stick or gel) is deemed to be transparent or clear if the maximum transmittance of light of any wavelength in the range 400 to 800 nm through a sample 1 cm thick is at least 35%, preferably at least 50%. The stick or gel is deemed translucent if the maximum transmittance of such light through the sample is between 2% and less than 35%. A stick or gel is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334A2.

The present invention contemplates a gel or stick composition, for reducing body malodor, using polyamide as the gelling agent in a cosmetically acceptable solvent from which the polyamide can solidify and form a gelled composition. The composition also includes active deodorant and/or antiperspirant ingredients, in a sufficient amount so as to have an effect to reduce body malodor. For example, where the active ingredient is a deodorant material (such as a deodorant fragrance and/or an antimicrobial agent), the composition should include the active deodorant material in sufficient amount so that after application to the skin malodor is reduced (this includes wherein a desired fragrance is increased).

The polyamide gellant will be further described in the following. Polyamides, under the generic name of nylon, are widely used as molding and extrusion compounds. Generally, these polyamides are thermoplastic polymers. Nylon plastics formed from hexamethylenediamine and adipic acid were first commercialized in 1941.

Typically, linear polyamides are formed from the condensation reaction of amino acid bifunctional monomers, or, alternatively, from the condensation of dibasic acids and diamines. Dicarboxylic acids fall within the dibasic acids which can be utilized for forming polyamides by condensation with diamines. Illustratively, the dicarboxylic acids are represented by the general formula HOOCRCOOH where R is a carbon chain having at least one carbon atom, illustratively 1–18 carbon atoms. The diamines are represented by the general formula $H_2NR'NH_2$, where R' is defined as above for R.

Polyamides are polymers that contain recurring amide groups as integral parts of the main polymer chains. If the polymers are formed by the condensation of diamines and dibasic acids, they are called AABB types, and can be represented by the general formula $H_2NRNH(COR'CONHRNH)_nCOR'COOR''$, where R and R' are defined as above, and R'' is either H or as defined above for R and R'. If a secondary diamine is used, the general formula above can be N-substituted with an R group. A common form of shorthand symbolism that serves to identify aliphatic polyamides is the use of numbers that signify the number of carbon atoms in the respective monomers. For AABB polymers, two numbers are used; the first gives the number of carbon atoms separating the nitrogen atoms of the diamines, and the second gives the number of straight-chain carbon atoms in the dibasic acids. For example, nylon-6,6 is prepared from hexamethylene diamine and adipic acid.

Polyamides prepared by the self-condensation of an amino acid are called type AB, with the general formula $H_2NRCO(NHRCO)_nNHRCOOR'$, where R is an aliphatic carbon chain of any number of carbon atoms, and R' can be R or H. This type of polyamide also uses a number system to identify the composition, but only a single number signifying the number of carbon atoms in the amino acid monomers is used. For example, nylon-6 is polycaprolactam, and nylon-12 is polylauryllactam.

One particular class of polyamides is especially useful in this invention. This class of polyamides is based on the condensation of (1) diamines with (2) relatively high molecular weight polybasic acids or esters, including dibasic acids or esters, which are obtained from thermal polymerization of a diene acid or ester, such as linoleic acid (for example, linoleates from soy bean, cotton seed or corn oils). The dibasic or polybasic acids are normally mixtures of materials. Typically, the largest component is a dibasic dimeric fatty acid possessing 18 carbon atoms per carboxyl group, but other mono-or polybasic fractions may be present. These mono- or polybasic acids may be a product of the polymerization of unsaturated vegetable oil acids or esters, or they can be deliberately added to the dimer acids, to modify the nature of the resulting polymer. The physical properties of polyamides of this type are determined to a large extent by the identity of the dimer acids used in their production. These polyamides are also called fatty polyamides, or polyamides from long-chain fatty acids (and esters). These polyamides have greater solubility in selected solvents and lower crystallinity than simpler nylons such as, for example, nylon-6,6 or nylon-6.

Examples of commercial polyamides which can be used as the polyamide gelling agent in the composition of the present invention are "Versamid" 1655 (by Henkel Corporation, CAS #68915-56-0), "Versamid" 744 (by Henkel Corporation, CAS #67989-30-4), "Uni-Rez" 2931 (by Union Camp Corporation, CAS #68139-80-0), "Macromelt" 6212 (by Henkel Corporation CAS #68650-50-0) and "Versamid" 930 (by Henkel Corporation, CAS #32131-17-2). Other commercial polyamides which can be used as the polyamide gelling agent include "Uni-Rez" 2658, "Uni-Rez" 2970, "Uni-Rez" 262 1, "Uni-Rez" 2613 "Uni-Rez" 2624, "Uni-Rez" 2665, "Uni-Rez" 1554, "Uni-Rez" 2623 "Uni-Rez", 2662, "Versamid" 1655, and "Versamid" 744. The "Uni-Rez" polyamides are by Union Camp Corporation, and the "Versamid" polyamides are by Henkel Corporation.

"Versamid" 1655 is prepared from dimers of $C_{18}$ unsaturated fatty acids which are partially hydrogenated, azelaic acid (nonanedioic acid), ethylene diamine, hexamethylene diamine and stearic acid. "Versamid" 744 is prepared from dimers of $C_{18}$ unsaturated fatty acids, ethylene diamine, hexamethylene diamine and propionic acid. "Uni-Rez" 2931 is prepared from dimers of $C_{18}$ unsaturated fatty acids, ethylene diamine and tall oil fatty acids. "Macromelt" 6212 is prepared from dimers of $C_{18}$ unsaturated fatty acids and diethylene diamine. "Versamid" 930 is prepared from adipic acid and hexylenediamine.

These examples of commercial polyamides are illustrative, and are not limiting of the present invention.

The foregoing polyamides are based on fatty acids. However, polyamide gelling agents for the present invention are not limited to those based on fatty acids. Illustratively, another class of polyamides that can be used to form gel or stick compositions according to the present invention are the "Elvamides" by DuPont, which are nylon multipolymer resins. These resins are water-white, transparent, soluble in alcohol/water or glycol solvents, and have a tendency to gel at high concentrations. For example, the resin is soluble in a 70/30 ethanol/water solution, and will gel in this solution for concentrations around 15% by weight resin.

This "Elvamide" class of polyamides is terpolymers with the components nylon-6, nylon-6,6 and nylon-6,10. This use of several monomer units gives these polyamides their increased solubilities. The CAS number is 25191-90-6.

Although we do not wish to be limited by any particular theory of gelation mechanism, we believe that gelation occurs in systems whose polyamide concentration exceeds a certain concentration (which will vary with solvent system, and which may, in some cases, be related to the concentration at which molecular overlap is achieved) at temperatures below the melting point of the polyamide resin. If each polymer chain, on the average, is involved in at least two different crystallites, a macroscopic 3-dimensional network is established, and the system acquires the dimensional stability of a solid. This gel structure is not permanent, as discussed previously.

As indicated previously, the polyamide is included in the composition in a sufficient amount such that the gelling agent as a whole gels and solidifies the composition to form a solid having a hardness of a gel or stick. Generally, lesser amounts of polyamide, without further gelling agents, will provide a gel composition, while increased amounts of the polyamide (or including co-gellants with the polyamide) can provide stick compositions. Illustratively, the polyamide is included in the composition in an amount of 2–40% by weight, of the total weight of the composition (preferably 6–20% by weight).

The solvent system, for dissolving the polyamide, can be a single solvent or a mixture of solvents. The solvent system can by hydrophilic or hydrophobic, depending upon the particular polyamide used, but preferably is as hydrophilic as possible. The polyamide can be dissolved in various monohydric or polyhydric alcohols, or other liquids (including silicone materials). The solvent can also be an emollient material, including a low polarity liquid emollient.

Polyhydric alcohols such as propylene glycol and dipropylene glycol are good solvents for the antiperspirant active ingredient, and some level thereof may be desirable to ensure clarity in the antiperspirant composition of the present invention. Furthermore, antiperspirant actives useful in the present invention often come supplied from the manufacturer in propylene glycol solutions. Thus, some polyhydric alcohol is preferable, but not required. Even where the antiperspirant active (e.g., an aluminum active material) is added in solid form, solid active can contain propylene glycol, e.g., in the inner coordination sphere of the aluminum. For example, aluminum chlorohydrate-propylene glycol complex will contain such propylene glycol, in an amount of 10–20% by weight propylene glycol, of the total weight of the active antiperspirant solid.

Incorporating a polyhydric alcohol solvent, in which the antiperspirant active material is dissolved, is desirable for providing a clear composition. However, good translucency (bordering on clarity) is possible without polyhydric alcohols, if solid antiperspirant is used and higher levels of surface active agents are used (for example, 10–15% by weight, of the total weight of the composition, of oleth-10 or similar surfactant). This is due to the fact that the solid antiperspirants containing glycols as part of the active powder are partially soluble in surface active agents.

The polyhydric alcohol, when used in the solvent system, can, illustratively, contain 2–12 carbon atoms and 2–8 hydroxyl groups. Examples of polyhydric alcohols are propylene glycol (propane-1,2-diol), butane-1,2-diol, butane-1,3-diol, dipropylene glycol, hexylene glycol, glycerol, tripropylene glycol and mixtures thereof. Illustratively, the polyhydric alcohol can be included in the composition in an amount of 5–70% by weight, of the total weight of the composition. Of course, as indicated previously, the solvent system need not include the polyhydric alcohol.

The solvent system also desirably includes a low polarity liquid emollient. Such liquid emollient can be selected from the group of unsaturated fatty alcohols, such as oleyl alcohol or ricinoleic alcohol (10–20 carbon atoms with 1, 2 or 3 double-bonds, the compound being branched or straight-chain); saturated fatty alcohols such as myristyl alcohol, lauryl alcohol, isolauryl alcohol, isostearyl alcohol, isocetyl alcohol, etc. (8–20 carbon atoms, branched or straight-chain); fatty and/or aromatic carboxylic acid esters such as benzyl benzoate, isostearyl benzoate, $C_{12}$–$C_{15}$ alkyl benzoate, $C_{10}$–$C_{15}$ alkyl lactate, isopropyl myristate, isopropyl palmitate, propyl myristate with the general formula RCOOR', where R and R' may be the same or not the same, and are from 2–20 carbon atoms, and may be saturated, unsaturated or aromatic; ethoxylated and/or propoxylated alcohols and acids such as PPG-14 myristyl ether, PPG-14 butyl ether, PPG-3 myristyl ether, myristeth-3 propionate, and similar materials known to those in the art; silicones such as cyclomethicones, dimethicones (50 to 1,000,000 cps) and functional silicones; mineral oil including non-volatile and volatile varieties; branched-chain hydrocarbons such as "Permethyl" (from Permethyl Corporation) and "Isopar" (from Exxon Corp.); and mixtures thereof. The low polarity liquid emollient is preferably in the composition in an amount up to 30% by weight, of the total weight of the composition; however, such low polarity liquid emollient is not required. The low polarity liquid emollient is generally hydrophobic in nature, and thus, it is preferred to also include surface active agents and/or polyhydric alcohols, when incorporating low polarity liquid emollients in the solvent system, in order to accommodate the antiperspirant active ingredient.

Desirably, the composition according to the present invention includes a surface active agent, to ensure rinsability of the formula. Illustrative agents including PEG-10 polyglyceryl-2 laurate, nonylphenol-10, PEG-100 stearate, and, more generally (although not limiting), emulsifiers that have an HLB (hydrophilic/lipophilic balance) value in the range of 3–18. The surfactant system is not limited to nonionic compounds, but can include blends (e.g., synergistic blends) with cationic or anionic surfactants which can provide emulsion stability, cosmetic application and skin feel properties.

The amount of active ingredient to be included in the composition can easily be determined, depending on the effect desired to be achieved. For example, where an antiperspirant material is incorporated in the composition, such material can be included in an amount, illustratively, of 4–30% by weight, of the total weight of the composition. Any of the astringent, acid metallic salts generally utilized in antiperspirant compositions can be utilized as part of antiperspirant compositions according to the present invention. Suitable active antiperspirant materials which may be mentioned by way of example include aluminum chlorohydrate, aluminum chloride, aluminum sesquichlorohydrate, zirconyl hydroxychloride, aluminum-zirconium hydroxychlorides, complexes or adducts of the above-mentioned active ingredients with glycols, such as propylene glycol (for example, "Rehydrol" II from Reheis Chemical Co.), and combinations thereof. Generally, any of the Category I-active antiperspirant ingredients listed in the Food and Drug Administration's Monograph on Antiperspirant Drug Products for Over-the-Counter Human Use (October 10, 1973) can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

As indicated previously, the composition according to the present invention can also include water, illustratively, in an amount of up to 30% by weight, of the total weight of the composition. However, water is not a required component.

Various optional ingredients which can be incorporated in the composition of the present invention, including auxiliary solidifying or gelling agents and coupling agents, have previously been discussed. The degree of freedom in incorporating optional ingredients is increased, where a clear composition is not being formed (for example, where a translucent or opaque composition is being formed).

Compositions according to the present invention can be made by mixing the various components at an elevated temperature and then cooling in order to form the gelled (solidified) composition (as a gel or stick). Desirably, any volatile components (such as fragrances) are added to the mixture at a relatively late stage of the mixing, so as to limit volatilization of the component. Generally, the solvent and polyamide gelling agent are mixed and heated so as to fully dissolve the polyamide in the solvent (illustrative temperatures of the heating are 35°–150° C.). An active ingredient (for example, active antiperspirant material) can be added after the polyamide fully dissolves, and mixing then takes place. Mixing continues with cooling, with, for example, color and fragrance then being added. Thereafter, the resulting composition is poured into canisters (e.g., dispensing packages) and solidified, as with conventional stick and gel compositions.

The compositions according to the present invention are used in the same manner as conventional gel or stick compositions, dispensed from, for example, dispensing canisters. For example, the gel or stick, exposed out of a dispensing package, is rubbed on skin, so as to deposit the active material (e.g., active deodorant and/or antiperspirant materials) on the skin. Illustratively, where the composition is an antiperspirant composition containing an active antiperspirant material, an exposed portion of the composition is rubbed against axillary regions of the human body, so as to deposit the active antiperspirant material on the skin in the axillary regions. As set forth previously, the gel or stick according to the present invention has good pay-off properties, so as to provide good depositing of the active antiperspirant material on the skin.

In the following, specific examples of compositions within the scope of the present invention are set forth. Of course, these specific examples are illustrative of the present invention, and are not limiting.

In the following examples, names utilized are the CTFA (Cosmetics, Toiletry and Fragrance Association, Inc.) names.

EXAMPLE I

The following sets forth the basic components of a preferred formulation:

|  | Parts by weight |
| --- | --- |
| Part I |  |
| Oleyl Alcohol | 20.00 |
| "Versamid" 930 (Polyamide) | 20.00 |
| PEG-10 Polyglyceryl-2 Laurate (HOES 3495) | 2.00 |
| Part II |  |
| Aluminum Zirconium Tetrachlorohydrate Glycine-PG Complex (36% in Propylene Glycol)-"Rezal" 36GPG | 33.30 |
| Dipropylene Glycol | 13.60 |
| Phenyl Trimethicone (Dow Corning Fluid 556) | 10.00 |
| Part III |  |
| Perfume | 1.00 |
| Color | 0.10 |
|  | 100.00 |

This formulation results in a transparent, firm, stable solid stick suitable for use in a commercial antiperspirant stick.

The above-listed components are formed into the composition by the following procedure. Oleyl alcohol and "Versamid" 930 are mixed and heated gradually with gentle agitation. The polyamide does not become fully soluble until the mixture reaches a temperature of about 220°614 225° F. This temperature of 220°–225° F. is maintained until all the polyamide dissolves. Thereafter, the PEG-10 polyglyceryl-2 laurate is added with slow agitation. The mixture is then cooled to 170°–180° F., and this temperature is maintained. In a separate vessel, the Part II ingredients are blended and mixed until homogeneous; thereafter, the Part II ingredients are added to the Part I ingredients with agitation, and cooling is continued with agitation. Thereafter, the color and fragrance is added, and the resulting mixture is poured into canisters at 100°–115° F.

EXAMPLE II

This example illustrates the use of aluminum chlorohydrate as an alternate active ingredient, to provide a transparent firm gel.

|  | Parts by weight |
| --- | --- |
| Part I |  |
| Oleyl Alcohol | 20.00 |
| "Versamid" 930 | 20.00 |
| PEG-10 Polyglyceryl-2 Laurate (HOES 3495) | 2.00 |
| Part II |  |
| "Rehydrol" II (36% soln in Propylene Glycol) (Aluminum Chlorohydrex-PG) | 33.30 |
| Phenyl Trimethicone (Dow Corning Fluid 556) | 23.70 |

| | Parts by weight |
|---|---|
| Part III | |
| Fragrance | 1.00 |
| | 100.00 |

EXAMPLE III

The following formula provides an opaque solid gel, that exhibits a tack-free feel on the skin.

| | Parts by weight |
|---|---|
| Part I | |
| "Versamid" 1655 | 15.00 |
| Oleyl Alcohol | 6.84 |
| Part II | |
| Cyclomethicone (Dow Corning Fluid 245) | 30.00 |
| Phenyl Trimethicone (Dow Corning Fluid 556) | 5.00 |
| Cyclomethicone and Dimethiconol (Dow Corning Fluid Q2 1401) | 2.00 |
| Part III | |
| Chlorohydrol (50% Aluminum Chlorohydrate in water) | 40.00 |
| Polysorbate 20 ("Tween" 20) | 0.30 |
| PEG-10 Polyglyceryl-2-Laurate (HOES 3495) | 0.80 |
| Color | 0.06 |
| | 100.00 |

The formulation of this example was prepared utilizing the following method. Initially, the components of Part I were mixed and heated, to 230° F. The silicone fluid blend (Part II) was then added to the Part I mixture, at 160° F. (after cooling the fully dissolved polyamide in the oleyl alcohol). The batch temperature was maintained at 155°–166° F., and the Part III blend was thereafter added to the mixture of the Parts I and II components while maintaining the temperature at 130°–140° F. After mixing thoroughly, the resulting mixture was poured into canisters and solidified.

EXAMPLE IV

This example illustrates the use of a glycol-based solvent system for a polyamide gellant. The formulation of this example is the following:

| | Parts by weight |
|---|---|
| Part I | |
| Hexylene Glycol | 20.55 |
| 1,3 Butylene Glycol | 1.67 |
| Dipropylene Glycol | 3.33 |
| "Versamid" 744 (Polyamide) | 20.00 |
| Part II | |
| Aluminum-Zirconium Tetrachlorohydrex Glycine-PG Complex ("Rezal" 36GPG 36% Soln. in PG) | 33.33 |
| Phenyl Trimethicone (Dow Corning Fluid 556) | 10.00 |
| Cyclomethicone | 5.00 |
| Cyclomethicone and Dimethiconol (Dow Corning Fluid Q2 1401) | 5.00 |

| | Parts by weight |
|---|---|
| Part III | |
| Fragrance | 1.00 |
| Color | 0.12 |
| | 100.00 |

The stick produced by the above formulation was translucent; however, the stick can be made clear by replacing all of the silicone materials, in Part II, with hexylene glycol, dipropylene glycol or blends of these glycols.

EXAMPLE V

The following formulation represents a clear antiperspirant stick. The following shows the function of each of the various components of the formulation in the composition.

| Ingredient | % by weight | Function |
|---|---|---|
| Part I | | |
| Oleyl Alcohol | 20.00 | Solvent |
| "Versamid" 930 | 20.00 | Gellant |
| Part II | | |
| PEG-10 Polyglyceryl-2 Laurate | 2.00 | Emulsifier |
| Part III | | |
| Aluminum-Zirconium Tetrachlorohydrex Glycine-PG Complex ("Rezal" 36 GPG (36% PG Soln)) | 33.30 | Active |
| Dipropylene Glycol | 13.60 | Co-solvent |
| Phenyl Dimethicone | 10.00 | Coupling agent |
| Part IV | | |
| Fragrance | 1.00 | Fragrance |
| Color (0.5% PG Soln) | 0.10 | Color |

The foregoing formulation was made utilizing the following procedure. Initially, the components of Part I were heated to 195° F. with gentle stirring, until the "Versamid" 930 dissolved in the alcohol. Thereafter, the solution was allowed to cool to 150° F. Then, the Part II component was added to the cooled Part I, and then Part III was added slowly with gentle mixing, while maintaining the temperature above 130° F. The resulting mixture was then poured into canisters at 125°–130° F., and allowed to gel. The resulting composition had a melting point of 61° C.

EXAMPLE VI

The following formulation is a clear antiperspirant stick composition using only glycols for the solvent system.

| Ingredient | % by weight |
|---|---|
| Hexylene Glycol | 26.67 |
| "Versamid" 744 | 20.00 |
| Aluminum Chlorohydrex PG Complex ("Rehydrol" –30% solution in DPG) | 43.33 |
| Dipropylene Glycol | 3.33 |
| 1,3-Butylene Glycol | 6.67 |
| | 100.00 |

The formulation of this example was made by the following procedure. Initially, the glycol materials were mixed and heated, to 185°–190° F. The "Versamid" 744 was then dissolved in the glycol mixture, and the antiperspirant active material (the "Rehydrol") was then added while maintaining the temperature at 150° F. The resulting mixture was then poured into canisters, and allowed to gel, providing a clear antiperspirant stick.

EXAMPLES VII–IX

The following formulations show translucent to clear antiperspirant sticks containing polyamide gellants and solubilized active. The amounts are in weight percent.

|  | Example VII | Example VIII | Example IX |
|---|---|---|---|
| $C_{12}$–$C_{15}$ Alkyl Lactate (Ceraphyl 41) | 25.0 | 27.36 | 27.36 |
| Cyclomethicone (Dow Corning Fluid 345) | 15.0 | 16.22 | 16.22 |
| "Uni-Rez" 2931 | 10.0 | 16.22 | 16.22 |
| 50% Aluminum Chlorohydrate (Chlorhydrol) (aq) | 15.9 | — | — |
| 50% Aluminum Chlorohydrex PG (Rehydrol) (in propylene glycol) | 34.1 | — | — |
| Glycerin | — | 10.0 | — |
| Water | — | 10.0 | 6.0 |
| Aluminum-Zirconium Tetrachlorohydrex Glycine-PG Complex ("Rezal" GPG) | — | 20.0 | 20.0 |
| Propylene glycol | — | — | 14.0 |
| Color (0.5% sol) | — | 0.2 | 0.2 |

EXAMPLES X–XI

The following formulations show antiperspirant sticks containing solid (powder) active which leave no visual residue. The amounts shown are in weight percent.

|  | Example X | Example XI |
|---|---|---|
| $C_{12}$–$C_{15}$ Alkyl Lactate (Ceraphyl 41) | 37.5 | 19.2 |
| Cyclomethicone (Dow Corning Fluid 345) | 15.0 | 11.4 |
| Octadecene Dimethyl Methyl Octadecyl Siloxane (Dow Corning 2503 Cosmetic Wax) | 15.0 | — |
| "Uni-Rez" 2931 | 7.5 | 11.4 |
| Aluminum-Zirconium Tetrachlorohydrate (AZP 701/Superfine (Reheis)) | 25.0 | — |
| Aluminum Chlorohydrex PG Complex (Rehydrol II (powder; Reheis)) | — | 23.5 |
| Oleth-10 | — | 18.5 |
| Water | — | 16.0 |

EXAMPLE XII

The following formulation is an opaque to slightly translucent antiperspirant stick which has improved aesthetic properties. The amounts shown are in weight percent.

|  | wt. % |
|---|---|
| "Uni-Rez" 2621 | 6.0 |
| Laureth-4 | 6.0 |
| Octyl Dodecyl Stearoyl Stearate | 4.0 |
| Aluminum-Zirconium Tetrachlorohydrex Glycine-PG Complex ("Rezal" 36GPG (in propylene glycol)) | 32.8 |
| Water | 3.0 |
| Distearyl Dimethyl Ammonium Chloride | 5.0 |
| Stearamidopropyl Cetearyl Dimonium Tosylate (and) Propylene Glycol | 8.0 |
| Dioctyl Cyclohexane | 9.6 |
| Dipropylene Glycol | 12.0 |
| Nonoxynol-9 (Igepal CO 630) | 7.6 |
| Cocomonoethanolamide | 5.0 |
| Perfume | 1.0 |

EXAMPLE XIII

This formulation shows a clear deodorant stick using a polyamide gelling agent:

|  | wt. % |
|---|---|
| "Uni-Rez" 2931 | 35 |
| Isocetyl alcohol | 64 |
| Fragrance | 1 |

EXAMPLE XIV

This formulation shows a translucent stick:

|  | wt. % |
|---|---|
| "Versamid" 1655 | 30 |
| Oleyl Alcohol | 70 |

EXAMPLE XV

This formulation shows an opaque paste (soft gel):

|  | wt. % |
|---|---|
| "Uni-Rez" 2931 | 10 |
| Hexylene glycol | 90 |

EXAMPLE XIV

The following formulation shows a clear gel:

|  | wt. % |
|---|---|
| "Uni-Rez" 2931 | 30 |
| Isolauryl alcohol | 70 |

The amounts shown in Examples XIII–XVI are in % by weight, of the total weight of the composition. Various cosmetic active materials (sunscreens, emollients, etc.) can be included in the cosmetic base of, e.g., Examples XIV–XVI, to provide cosmetic materials achieving the objectives of the present invention.

Thus, according to the present invention a stick or gel composition having good pay-off and application properties, and having good structural integrity, can be achieved. Furthermore, clear compositions, including clear antiperspirant gel or stick compositions, can be achieved. In addition, the compositions according to the present invention are stable, the gellant being stable even in the presence of an antiperspirant metal salt, such as conventional acidic antiperspirant metal salts like aluminum chlorohydrate or aluminum-zirconium tetrachlorohydrex-Gly. In addition, the compositions according to the present invention can be easily manufactured, and the compositions are reversible (that is, the compositions can be melted and re-cast in molds without change in overall properties). Furthermore, the compositions have low residue characteristics.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A composition for reducing body malodor, comprising:
   (1) an active ingredient selected from the group consisting of active deodorant materials and active antiperspirant materials, in an amount effective to reduce body malodor;
   (2) a polyamide as a gelling agent for the composition, the gelling agent being included in a sufficient amount such that the composition is a solid composition; and
   (3) a solvent system for the polyamide, in an amount such that the polyamide can be dissolved therein, and the polyamide can be gelled therefrom upon cooling, the composition being a gel or stick.

2. A composition according to claim 1, wherein the composition includes 2%–40% by weight, of the total weight of the composition, of the polyamide, and includes 10%–95% by weight, of the total weight of the composition, of the solvent system.

3. A composition according to claim 2, wherein the active ingredient is included in the composition in an amount of 0.1%–30% by weight, of the total weight of the composition.

4. A composition according to claim 2, wherein the active ingredient includes an active deodorant material, in an amount effective to reduce body malodor.

5. A composition according to claim 2, wherein the active ingredient includes an active antiperspirant material, in an amount effective to reduce production of perspiration by a body, whereby an antiperspirant composition is provided.

6. An antiperspirant composition according to claim 5, wherein the antiperspirant composition is clear.

7. An antiperspirant composition according to claim 5, wherein the antiperspirant composition includes 4%–30% by weight, of the total weight of the composition, of the active antiperspirant material.

8. An antiperspirant composition according to claim 7, wherein the composition further includes a surface active agent, in sufficient amount to ensure rinsability of the composition from skin.

9. An antiperspirant composition according to claim 8, wherein the solvent system includes a polyhydric alcohol containing 2–12 carbon atoms and 2–8 hydroxyl groups, the polyhydric alcohol being included in the composition in an amount of 5%–70% by weight of the total weight of the composition.

10. An antiperspirant composition according to claim 9, wherein the solvent system further includes a low polarity liquid emollient, in an amount up to 30% by weight of the total weight of the composition.

11. An antiperspirant composition according to claim 7, wherein the polyamide is a neutral polyamide.

12. An antiperspirant composition according to claim 7, wherein the polyamide is a polyamide formed from the condensation reaction of amino acid bifunctional monomers.

13. An antiperspirant composition according to claim 7, wherein the polyamide is a polyamide formed from a condensation reaction of dibasic acids and diamines.

14. An antiperspirant composition according to claim 13, wherein said dibasic acids include a dibasic dimeric fatty acid.

15. An antiperspirant composition according to claim 14, wherein said dibasic dimeric fatty acid is a dibasic dimer of linoleic acid.

16. An antiperspirant composition according to claim 13, wherein the diamines are fatty diamines.

17. An antiperspirant composition according to claim 7, wherein the polyamide is a terpolymer with the components nylon-6, nylon-6,6 and nylon-6,10.

18. An antiperspirant composition according to claim 7, wherein the polyamide is selected from the group consisting of a first polyamide prepared from dimers of $C_{18}$ unsaturated fatty acids which are partially hydrogenated, azelaic acid (nonanedioic acid), ethylenediamine, hexamethylenediamine and stearic acid; a second polyamide prepared from dimers of $C_{18}$ unsaturated fatty acids, ethylenediamine, hexamethylenediamine and propionic acid; a third polyamide prepared from dimers of $C_{18}$ unsaturated fatty acids, ethylenediamine and tall oil fatty acids; a fourth polyamide prepared from dimers of $C_{18}$ unsaturated fatty acids and diethylenediamine; and a fifth polyamide prepared from adipic acid and hexylenediamine.

19. An antiperspirant composition according to claim 7, wherein the composition is a stick composition.

20. An antiperspirant composition according to claim 7, wherein the composition is a gel composition.

21. An antiperspirant composition according to claim 7, wherein the composition is a clear composition.

22. An antiperspirant composition according to claim 7, wherein the polyamide forms a continuous phase in the composition, the active antiperspirant material being dispersed throughout the continuous phase.

23. An antiperspirant composition according to claim 7, wherein the polyamide forms a continuous phase in the composition, and wherein the active antiperspirant material is dissolved in the continuous phase.

24. An antiperspirant composition according to claim 5, wherein the active antiperspirant material includes an acidic antiperspirant metal salt.

25. An antiperspirant composition according to claim 24, wherein the acidic antiperspirant metal salt is on acidic antiperspirant aluminum salt.

26. An antiperspirant composition according to claim 24, wherein the antiperspirant composition includes 4%–30% by weight, of the total weight of the composition, of the active antiperspirant material.

27. An antiperspirant composition according to claim 5, wherein the active antiperspirant material is an acidic active antiperspirant material.

28. An antiperspirant composition according to claim 5, consisting essentially of said active antiperspirant material, said gelling agent and said solvent system.

29. An antiperspirant composition according to claim 5, further including active deodorant materials.

30. An antiperspirant composition according to claim 29, consisting essentially of said active antiperspirant material, said active deodorant materials, said gelling agent and said solvent system.

31. A composition according to claim 1, further including an additional gelling agent, provided in an amount, together with the polyamide, such that the composition is a gel composition or a stick composition.

32. A composition according to claim 1, wherein the composition is a clear composition.

33. A composition according to claim 1, wherein the solvent system includes a polyhydric alcohol containing from 2–12 carbon atoms and from 2–8 hydroxyl groups.

34. A composition according to claim 1, wherein the solvent system includes an unsaturated fatty alcohol, having 10–20 carbon atoms and 1–3 double bonds.

35. A composition according to claim 34, wherein the solvent system also includes a polyhydric alcohol containing from 2–12 carbon atoms and from 2–8 hydroxyl groups.

36. A composition according to claim 1, wherein the polyamide is a neutral polyamide.

37. A composition according to claim 36, wherein the polyamide is a polyamide formed from the condensation reaction of amino acid bifunctional monomers.

38. A composition according to claim 36, wherein the polyamide is a polyamide formed from a condensation reaction of dibasic acids and diamines.

39. A method of reducing body malodor of a person, comprising the step of applying said composition of claim 1 to skin of the person.

40. The method according to claim 39, wherein said composition is applied to axillary regions of the person, so as to reduce body malodor from the axillary regions.

41. A method of reducing body malodor of a person, comprising the step of applying said composition of claim 5 to skin of the person, so as to reduce perspiration.

42. The method according to claim 41, wherein said composition is applied to axillary regions of the person, so as to reduce perspiration from the axillary regions.

43. A composition according to claim 1, wherein the polyamide is selected from the group consisting of terpolymers that are soluble in said solvent system and polyamides based on dimerized fatty acids.

44. A composition according to claim 43, wherein the polyamide is a polyamide based on dimerized fatty acids.

45. A composition according to claim 44, wherein the polyamide based on dimerized fatty acids is a polyamide formed by condensation polymerization of dimerized fatty acids with difunctional amines.

46. A composition according to claim 1, wherein the composition is a gel system that forms the solid composition upon cooling, and can be brought to a fluid state by heating the solid composition.

47. A composition according to claim 36, wherein the neutral polyamides have a molecular weight on the range of 1,000 to 30,000 daltons as measured by gel permeation chromatography.

48. A composition according to claim 1, wherein the solvent system further includes a low polarity liquid emollient.

49. A solid antiperspirant composition, comprising:
(a) 2–40% by weight, of the total weight of the composition, of a polyamide gelling agent, which is a solid in the composition;
(b) 10–95% by weight, of the total weight of the composition, of a solvent for the polyamide gelling agent;
(c) 0–50% by weight, of the total weight of the composition, of a surface active agent to ensure rinsability of the composition from human skin;
(d) 4–30% by weight, of the total weight of the composition, of an antiperspirant active ingredient; and
(e) 0–30% by weight, of the total weight of the composition, of water, wherein the composition is a gel or stick.

* * * * *